United States Patent
Noguchi et al.

(12) 
(10) Patent No.: US 6,511,536 B1
(45) Date of Patent: Jan. 28, 2003

(54) PIGMENT IN THIN FLAKES COATED WITH CALCIUM CARBONATE AND A METHOD FOR MANUFACTURING THE SAME

(75) Inventors: Tamio Noguchi, Fukushima-ken (JP); Yukitaka Watanabe, Fukushima-ken (JP)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/629,088

(22) Filed: Jul. 31, 2000

(30) Foreign Application Priority Data

Jul. 29, 1999 (JP) ............................................. 11-214925
Sep. 1, 1999 (JP) ............................................. 11-247168

(51) Int. Cl.⁷ ............................ C04B 14/20; C09C 1/04; C09C 1/02; A61K 7/021; A61K 7/035
(52) U.S. Cl. ..................... 106/417; 106/424; 106/463; 106/464; 106/465; 424/63; 424/69
(58) Field of Search ................................. 106/417, 424, 106/463–465; 424/63, 69

(56) References Cited

U.S. PATENT DOCUMENTS

| | | | | |
|---|---|---|---|---|
| 3,925,095 A | * | 12/1975 | Bockmann et al. | 106/308 N |
| 4,603,047 A | * | 7/1986 | Watanabe et al. | 424/63 |
| 5,169,442 A | * | 12/1992 | Noguchi et al. | 106/417 |
| 5,910,214 A | * | 6/1999 | You | 106/465 |
| 6,136,085 A | * | 10/2000 | Adams, Jr. et al. | 106/463 |

* cited by examiner

Primary Examiner—Mark L. Bell
Assistant Examiner—Patricia L. Hailey
(74) Attorney, Agent, or Firm—Millen, White, Zelano & Branigan, P.C.

(57) ABSTRACT

Pigments of flake substrate coated with calcium carbonate wherein the surface of the flake substrate is coated with fine particles of calcium carbonate. The pigment may be manufactured by a method where calcium carbonate in fine particles is separated out and coated on the surface of the flaky substrate by the reaction of a calcium salt with a carbonate in a suspension of the flake substrate. It can be used as an extender particularly for cosmetics exhibiting appropriate adhesion to skin, low luster and excellent wrinkle-hiding effect, prevention of unpleasant feel due to perspiration, sebum absorbing property, etc.

13 Claims, No Drawings

PIGMENT IN THIN FLAKES COATED WITH CALCIUM CARBONATE AND A METHOD FOR MANUFACTURING THE SAME

The present invention relates to a novel pigment in thin flakes coated with calcium carbonate. More particularly, it relates to a novel pigment of flakes coated with calcium carbonate which exhibits appropriate adhesion to skin, low luster and excellent wrinkle-hiding effect, prevention of unpleasant feel due to perspiration and sebum, absorption which are particularly useful in the cosmetic field.

BACKGROUND OF THE INVENTION

Up to now, in the cosmetic field, inorganic powders such as natural mica, synthetic mica, talc, sericite and silica flakes have been used as extenders. However, they are not sufficient in terms of the functions desired in cosmetics such as adhesion to skin, spread, wrinkle-hiding effect, etc. For example, when natural mica is used as an extender, luster results and adhesion to the skin is strong, both rendering it unsatisfactory. Talc is not preferred since it may contain asbestos therein. In addition, it provides excessive sliding and its "settlement" ( i.e., the extent when applied to the skin, of satisfactory sliding in the initial stage and setting in the final stage), recently desired in cosmetics, is poor.

For example, in the case of an oil foundation containing mica, there are problems in view of unnatural high luster and of spread. In the case of mica which is coated with fine particles of titanium oxide, as compared with mica, both adhesion and spreadability are improved and better feel on skin is achieved. However, reflection of light at the layer coated with titanium oxide is high and, therefore, when the compounding amount in the foundation is increased, luster becomes high. In addition, when it is applied to the skin, luster, a reduction in masking property, degeneration of the make-up, etc. result due to perspiration and sebum secretion and they may cause a reduction of good maintenance of the make-up. Accordingly, its compounding amount with cosmetics has to be limited.

Therefore, there has been a demand especially in the cosmetic field for development of extenders where luster is appropriately controlled and spreadability and adhesion are good.

SUMMARY OF THE INVENTION

The inventors have carried out an intensive investigation for solving the above problems concerning extenders for cosmetics and have found that, when an extender having calcium carbonate coated on the surface of a flaky substrate is compounded with cosmetics such as foundation, both appropriate adhesion and spread can be achieved. Further, such extender does not express excessive luster as with mica but has a good characteristic as an extender for cosmetics where the luster is suppressed.

Thus, the present invention provides a novel pigment of thin flakes coated with fine particles of calcium carbonate, a method for manufacturing the same and cosmetics, plastic compositions, paint compositions and ink compositions containing the pigment. Preferred, but not limiting embodiments of the invention include the following (1)–(9).

(1) A pigment of thin flake substrate coated with calcium carbonate where fine particles of calcium carbonate are coated on the surface of the flake substrate;

(2) The pigment in thin flakes coated with calcium carbonate according to (1), wherein fine particles of calcium carbonate are coated in an amount of 5–70% by weight to the total amount of the pigment;

(3) The pigment in thin flakes coated with calcium carbonate according to (1) or (2), wherein the average particle size of the flake substrate is 0.5–50 $\mu$m;

(4) The pigment in thin flakes coated with calcium carbonate according to any of (1)–(3), wherein the average particle size of calcium carbonate is 200 nm or smaller;

(5) The pigment in thin flakes coated with calcium carbonate according to any of (1)–(5), wherein the pigment is treated with an organic compound;

(6) A method for the manufacture of a pigment of thin flakes coated with calcium carbonate, characterized in that, an aqueous solution of calcium salt and an aqueous solution of a carbonate are added to a suspension of a flake substrate with stirring so that calcium carbonate is coated as fine particles on the surface of the flake substrate, preferably followed by filtering, washing and drying;

(7) The method for the manufacture of a pigment in thin flakes coated with calcium carbonate according to (6), wherein a complex-forming agent is added in the coating treatment with fine particles of calcium carbonate;

(8) A cosmetic agent where the pigment in thin flakes coated with calcium carbonate according to any of (1)–(5) is contained therein; and (9) A plastic composition, a paint composition or an ink composition where the pigment in thin flakes coated with calcium carbonate according to any of (1)–(5) is contained therein.

Upon further study of the specification and appended claims, further objects and advantages of this invention will become apparent to those skilled in the art.

The present invention will now be illustrated in further detail.

Particle size of the flake substrate used in the present invention refers to the average size of the particles' largest dimension and is preferably within a size of 0.5–50 $\mu$m with the particle size of 0.5–20 $\mu$m being particularly preferred. The average particle thickness is preferably within a range of 0.01–1.0 $\mu$m and, particularly preferably, it is 0.02–0.05 $\mu$m. When the particle size is larger than 50 $\mu$m, luster becomes disadvantageously high, whereby control of luster according to the invention is difficult. In addition, feel on use, such as appropriate adhesion, spreadability and smoothness on the skin surface, is deteriorated. The result is poor adaptability as an extender for cosmetics. There is no particular limitation as to the material for the flake substrate so far as it has a desired flake shape. Natural mica, talc, sericite, synthetic mica, silica flakes, alumina flakes, kaolin, mica coated with titanium oxide, mica coated with iron oxide, mica coated with barium sulfate, mica coated with titanium oxide and with barium sulfate and bismuth oxychloride may be exemplified. Usually, mica is preferred.

Now, a method for the manufacture of the pigment in thin flakes coated with calcium carbonate will be described. First, a suspension of the flake substrate is warmed and, with stirring, an aqueous solution of a calcium salt and an aqueous solution of a carbonate are added to this suspension. The reaction temperature at that time is appropriately selected, preferably from 20° C. (ambient temperature) to 60° C., by taking in to consideration the concentration and rate of addition of the aqueous solution of the calcium salt to be added, the growing speed of the calcium carbonate crystals and/or the size of the desired calcium carbonate coating produced. When a calcium salt having a low solubility in water is used, the aqueous solution of a calcium salt to be added may be prepared by dissolving it beforehand with the aid of hydrochloric acid or the like.

A favorable result may sometimes be achieved in the above coating treatment if a complex-forming agent for forming a complex with calcium is added. This can allow control of the size and the shape of the calcium carbonate coating particles. Examples of the complex-forming agent used therefore are oxalic acid, citric acid, tartaric acid, EDTA, sodium citrate and salts thereof. As a result of the present reaction operation, calcium carbonate is produced by the reaction of the calcium salt with the carbonate and is coated on the surface of the flake substrate as fine particles. The flake substrate coated with the fine particles of calcium carbonate is filtered, washed and dried, preferably at 100–150° C. If desired, the dried final pigment may be calcined at not higher than the decomposing point of calcium carbonate (600° C.). Examples of the calcium salt used in this coating step are calcium chloride and calcium nitrate and the use of calcium chloride is preferred. Examples of the carbonate are sodium carbonate and potassium carbonate and the use of sodium carbonate is preferred.

As a result of X-ray diffraction, it has been confirmed that the calcium carbonate particles which are coated on the surface of the flake substrate as described above are in a crystalline form of a calcite type or an aragonite type. As to the use as an extender, there is almost no difference in the characteristics between one of these single crystalline forms and a mixed system of those crystalline forms. Preferred particle size of the calcium carbonate is 0.4 $\mu$m or smaller, particularly 200 nm or smaller. Although there is no particular limitation for the coating amount, a preferred amount is 1–80% by weight (to the total amount of coated pigment), particularly, 5–70% by weight (to the total amount of coated pigment). The pigment in thin flakes coated with calcium carbonate in accordance with the present invention is advantageous in that adhesion on the skin surface is appropriate and feel on use such as spreadability and smoothness is excellent.

When the pigment in thin flakes coated with calcium carbonate of the present invention is intended to be compounded with cosmetics, it may be subjected to an organic compound treatment to prevent aggregation and improve dispersibility. Preferred agents for the treatment include, metal soaps, amine salts thereof, silicone compounds, fluorine compounds, fatty acids; surface-active agents, natural substance or mixtures thereof. Examples of the metal soaps are aluminum stearate, zinc stearate, magnesium stearate and diethanolamine stearate. Examples of the silicone compounds are the silicones which are customarily used for cosmetics (for example, alkyl hydrogen polysiloxanes such as methyl hydrogen polysiloxane, ethyl hydrogen polysiloxane and propyl ethyl hydrogen polysiloxane manufactured and sold by Toray-Dow, Shin-Etsu Silicone, etc.). Examples of the fluorine compounds are various kinds of surface-active agents of a fluorine type. Examples of the fatty acids are caproic acid, caprylic acid, lauric acid, stearic acid and arachic acid. Examples of the surface-active agents are polyethylene glycol, polypropylene glycol, HEC, HPC and CMC. And examples of the natural substance are gelatin, glue, collagen, casein, chitin, chitosan and alginic acid. The above treating agent may be used by means of any of a dry mixing method, where the agent is directly added to the powder using a Henschel mixer or the like and subjected to a dry mixing, and a mixing method where the agent is previously dissolved in a solvent which dissolves the agent, such as water or alcohol, and the solution is added to the pigment to be treated followed by evaporating and drying.

There is no particular limitation for the cosmetics with which the pigment in thin flakes coated with calcium carbonate according to the present invention can be compounded. Examples are cosmetics for make-up, hair and bath agents, foundations, milky lotions, lipsticks, mascaras and manicures. There is no particular limitation on the compounding amount and, depending upon the type and the object for use thereof, it is compounded appropriately in an amount of 1–50% by weight. At that time, in addition to the pigment in thin flakes coated with calcium carbonate of the present invention, other components which are usually used as additives to cosmetics may be compounded therewith.

Examples of the other components are inorganic pigments such as natural mica, mica coated with titanium oxide, mica coated with iron oxide, bismuth oxychloride, synthetic mica, talc, kaolin, sericite, magnesium carbonate, silica, zeolite, hydroxyapatite, titanium oxide, red iron oxide, yellow iron oxide, black iron oxide, zinc oxide, metal powder, prussian blue, ultramarine, carbon black, chromium oxide, cobalt titanate and glass beads; organic pigments such as nylon beads and silicone beads; organic pigments such as Red No. 201, Red No. 202, Red No. 226, Red. No. 205, Red No. 228, Red No. 405, Yellow No. 205, Yellow No. 401, Blue No. 404, Blue No. 1 and Orange No. 205; hydrocarbons such as squalane, liquid paraffin, palmitic acid, stearic acid, bees wax and myristyl myristate; and organic solvents such as acetone, toluene, butyl acetate and other acetates. Other examples are surface-active agents, ultraviolet absorbers, antioxidants, antiseptics, polyhydric alcohols and perfumes.

The pigment in thin flakes according to the present invention is not limited to cosmetics only but may be used in other applications as a pigment, a filler, etc. For example, it may be used in plastic compositions, paint compositions, ink compositions, as fillers for paper manufacturing, etc.

In the case of use in plastic compositions, the use for the following resins may be exemplified: thermoplastic resin such as polyolefins (e.g., polyethylene, polystyrene and polypropylene), polyvinyl chloride, polyvinylidene chloride, polyacetal, acrylic, polyacrylate, polymethacrylate, polyester and ABS; and thermosetting resins such as epoxy, phenol, polyether, melamine, ultraviolet ray-curable resin, unsaturated polyester, amino, aniline, furan and silicone. Other examples are polyamide, polyimide, fluorine, polyethylene terephthalate, polybutylene terephthalate and polycarbonate.

With regard to the utilization in paints, it is possible to use in paint for automobiles, for example. Its usage form may, for example, be any of a solvent type, an aqueous type and an emulsion type. The pigment in thin flakes coated with calcium carbonate according to the present invention may be used either solely or jointly together with coloring pigment, organic pigment, inorganic pigment, brilliant pigment, and metal pigment such as titanium oxide, red iron oxide, yellow iron oxide, black iron oxide, carbon black, aluminum pigment, mica coated with titanium oxide and alumina pigment.

With regard to the use in ink, it may be printed as a printing ink for example, on paper, plastic sheet, etc. It may be used in offset printing, gravure printing, flexographic printing, screen printing, etc. The pigment in thin flakes coated with calcium carbonate according to the present invention may be used in combination with other coloring materials as well.

The pigment of the present invention may also be used as a filler in paper manufacturing. For example, it is possible that the pigment of the present invention is mixed with wood pulp, then starch, sizing agent, paper reinforcing agent, etc. are added thereto and the mixture is made into paper followed by drying whereupon paper is manufactured. It is also possible to use other fillers, talc, etc. at that time.

The entire disclosure of all applications, patents and publications, cited above and below, and of corresponding Japanese Patent Application Nos. JP 11-214,925, filed Jul. 29, 1999 and JP 11-247,168, filed Sep. 1, 1999 is hereby incorporated by reference.

EXAMPLE

In the foregoing and in the following examples, all temperatures are set forth uncorrected in degrees Celsius; and, unless otherwise indicated, all parts and percentages are by weight.

Example 1

White mica (1,128 g) having a particle size of 1–15 μm was suspended in 6.0 liters of water. This suspension was heated at 55° C. with stirring. A 10% by weight aqueous solution of sodium carbonate was added thereto to adjust the pH of the suspension to 10.8. After that, a solution prepared by dissolving 528 g of calcium chloride dihydrate and 18 ml of hydrochloric acid in 3.0 liters of water and a 10% by weight aqueous solution of sodium carbonate were dropped thereinto simultaneously. After completion of the dropping, the product was filtered, washed with water and dried at 110° C. As a result, a pigment coated with 22.6% by weight of fine particles of calcium carbonate was obtained. Physical properties of the resulting pigment are given in Table 1.

From the MIU data, the mica coated with calcium carbonate was confirmed to have an appropriate adhesion and a low luster as compared with mica or titanium oxide-coated mica.

Example 2

White mica (1,000 g) having a particle size of 1–15 μm was suspended in 5.6 liters of water. This suspension was heated at 40° C. with stirring. Citric acid monohydrate (20 g) was added to and dissolved in this suspension, then a 20% by weight aqueous solution of potassium carbonate was added thereto to adjust the pH of the suspension to 6.5, and a solution prepared by dissolving 980 g of calcium chloride dihydrate and 40 ml of hydrochloric acid in 4.0 liters of water and a 20% by weight aqueous solution of potassium carbonate were dropped thereinto simultaneously. After completion of the dropping, the product was filtered, washed with water and dried at 110° C. As a result, a pigment coated with 40% by weight of fine particles of calcium carbonate was obtained. Physical properties of the resulting pigment are given in Table 1.

From the MIU data, the mica coated with calcium carbonate was confirmed to have an appropriate sliding property and a low luster as compared with mica titanium.

TABLE 1

The physical properties of this invented pigment and titanium oxide coated on mica

| Sample | Luster (60°/60°) | Whiteness | hiding power | MIU (*2) | Oil absorption (ml/100 g) |
|---|---|---|---|---|---|
| Example 1 | 7.0 | 89.3 | 6.0 | 0.76 | 85 |
| Example 2 | 6.5 | 90.8 | 6.8 | 0.68 | 110 |

TABLE 1-continued

The physical properties of this invented pigment and titanium oxide coated on mica

| Sample | Luster (60°/60°) | Whiteness | hiding power | MIU (*2) | Oil absorption (ml/100 g) |
|---|---|---|---|---|---|
| Titanium oxide coated mica (*1) | 13.0 | 92.7 | 48.4 | 0.78 | 85 |

(*1) ultra fine TiO2 particles (22.6 weight %) coated on the surface of the mica having particle size of 1–15 μm
(*2) The measured value of the mean frictional coefficient (MIU) as measured by "Frictional Feel Tester, type KES-SE-DC manufactured by Katotech KK".

Example 3

The following are application examples where the pigment in thin flakes coated with calcium carbonates obtained by the present invention are used.

1. Use Examples as Cosmetics.
A: Formulation for Compact Powder
(Composition)

| | |
|---|---|
| Pigment obtained in Example 1 or Example 2 | 25 parts by weight |
| Coloring pigment | 5 parts by weight |
| Lanolin | 3 parts by weight |
| Isopropyl myristate | q.s. |
| Magnesium stearate | 2 parts by weight |
| Talc | 50 parts by weight |

B: Formulation for Foundation
(Composition)

| | |
|---|---|
| Pigment obtained in Example 1 or Example 2 | 25 parts by weight |
| Talc (JA-46R; manufactured by Asada Talc) | 38 parts by weight |
| Mica (average particle size: 8 μm) | 10 parts by weight |
| Magnesium stearate | 3 parts by weight |
| Nylon powder 12 | 8 parts by weight |
| Yellow iron oxide | 1.9 parts by weight |
| Red iron oxide | 0.8 part by weight |
| Titanium oxide | 1.0 part by weight |
| Mineral oil (70) | q.s. |
| (Caprylic/capric) triglyceride | 3.3 parts by weight |
| Butyl paraben | 0.1 part by weight |

C: Formulation for Lipstick

| | |
|---|---|
| Pigment of Example 1 or 2 | 7 parts by weight |
| Coloring pigment | 2 parts by weight |
| Carnauba wax | 2 parts by weight |
| Ceresine | 7 parts by weight |
| Liquid paraffin | 5 parts by weight |
| Vaseline | 8 parts by weight |
| Castor oil | q.s |
| Perfume | q.s |

The above composition was mixed and molded to prepare a lipstick.

2. Use Example as Paint (for Automobiles)
(Composition A) (Acrylmelamine resin)

| | |
|---|---|
| Acrydic 47-712 | 70 parts by weight |
| Superdeccamine G821-60 | 30 parts by weight |

(Composition B)

| | |
|---|---|
| Pigment obtained in Example 1 or Example 2 | 10 parts by weight |
| Pearl pigment | 10 parts by weight |

(Composition C) (Thinner for acrylmelamine resin)

| | |
|---|---|
| Ethyl acetate | 50 parts by weight |
| Toluene | 30 parts by weight |
| n-Butanol | 10 parts by weight |
| Solvesso #150 | 40 parts by weight |

The composition A (100 parts by weight) was mixed with 20 parts by weight of the composition B and the mixture was diluted with the composition C to adjust to a viscosity (12–15 sec. in # 4 Ford cup) suitable for a spray coating and subjected to a spray coating to form a base coat layer.

3. Use Example to Plastics
Composition (Plastic composition)

| | |
|---|---|
| High-density polyethylene (pellets) | 100 parts by weight |
| Pigment obtained in Example 1 or Example 2 | 1 part by weight |
| Magnesium stearate | 0.1 part by weight |
| Zinc stearate | 0.1 part by weight |

The pellets according to the above compounding ratio were subjected to a dry blending and then subjected to an injection molding.

4. Use Example to Ink

| | |
|---|---|
| CCST Medium (a resin of a nitrocellulose type; manufactured by Toyo Ink) | 10 parts by weight |
| Pigment obtained in Example 1 or Example 2 | 8 parts by weight |

NC 102 solvent (manufactured by Toyo Ink) was added to an ink composition according to the above formulation and the viscosity of the mixture was adjusted to 20 seconds using a Zahn cup No. 3 to prepare a printing ink.

What is claimed is:

1. A pigment comprising a flake substrate selected from the group consisting of mica, talc, sericite, synthetic mica, silica flakes, alumina flakes, kaolin, mica coated with titanium oxide, and mica coated with iron oxide, wherein said flake substrate is coated with particles of calcium carbonate on the surface, wherein the particles of calcium carbonate have an average particle size of 0.4 $\mu$m or smaller.

2. The pigment of claim 1, wherein the particles of calcium carbonate are coated in an amount of 1–80% by weight based on the total weight of the pigment.

3. The pigment of claim 1, wherein the particles of calcium carbonate are coated in an amount of 5–70% by weight based on the total weight of the pigment.

4. The pigment of claim 1, wherein the average particle size of the flake substrate is 0.5–50 $\mu$m.

5. The pigment of claim 1, wherein the average particle size of the particles of calcium carbonate is 200 nm or smaller.

6. A cosmetic composition comprising a pigment according to claim 1.

7. A cosmetic composition of claim 6, wherein the pigment is contained in an amount of 1–50% by weight of the total composition.

8. A plastic composition, a paint composition or an ink composition comprising a pigment according to claim 1.

9. A pigment comprising a flake substrate coated with particles of calcium carbonate on the surface, wherein the particles of calcium carbonate have an average particle size of 0.4 $\mu$m or smaller, and wherein the pigment is treated with an organic compound.

10. The pigment of claim 9, wherein the organic compound is a metal soap, an amine salt of a metal soap, a silicone compound, a fluorine compound, a fatty acid, a surface-active agent, a natural substance or a mixture thereof.

11. A method for preparing a pigment comprising a flake substrate coated with calcium carbonate, which method comprises adding an aqueous solution of calcium salt and an aqueous solution of a carbonate to a suspension of a flake substrate selected from the group consisting of mica, talc, sericite, synthetic mica, silica flakes, alumina flakes, kaolin, mica coated with titanium oxide, and mica coated with iron oxide, with stirring so that calcium carbonate is coated as particles having an average particle size of 0.4 $\mu$m or smaller on the surface of the flake substrate, followed by filtering, washing and drying.

12. A method for preparing a pigment comprising a flake substrate coated with calcium carbonate, which method comprises adding an aqueous solution of calcium salt and an aqueous solution of a carbonate to a suspension of a flake substrate with stirring so that calcium carbonate is coated as particles having an average particle size of 0.4 $\mu$m or smaller on the surface of the flake substrate, followed by filtering, washing and drying, wherein a complex-forming agent is added in the coating treatment with fine particles of calcium carbonate.

13. A method for preparing a pigment comprising a flake substrate coated with calcium carbonate, which method comprises adding an aqueous solution of calcium salt and an aqueous solution of a carbonate to a suspension of a flake substrate with stirring so that calcium carbonate is coated as particles having an average particle size of 0.4 $\mu$m or smaller on the surface of the flake substrate, followed by filtering, washing and drying, wherein the aqueous solution of calcium salt contains hydrochloric acid.

* * * * *